United States Patent
Montgomery (10) Patent No.: US 6,736,836 B2
(45) Date of Patent: May 18, 2004

(54) TRANSPLANT ORGAN EXTERNAL COOLING SYSTEM

(75) Inventor: Robert A Montgomery, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/788,309

(22) Filed: Feb. 16, 2001

(65) Prior Publication Data

US 2001/0025191 A1 Sep. 27, 2001

Related U.S. Application Data (60) Provisional application No. 60/183,093, filed on Feb. 17, 2000.

(51) Int. Cl.⁷ .................................................. A61F 7/00
(52) U.S. Cl. ........................................ 607/104; 62/306
(58) Field of Search ........................... 62/306, 78, 457; 435/284.1, 1; 607/104; 128/400; 219/506

(56) References Cited

U.S. PATENT DOCUMENTS

| | | | |
|---|---|---|---|
| 3,091,242 A | 5/1963 | Johnson, Jr. et al. ....... 128/402 |
| 3,717,199 A | 2/1973 | Dienst .......................... 165/46 |
| 3,810,367 A | 5/1974 | Peterson ...................... 62/457 |
| 4,154,245 A | 5/1979 | Daily .......................... 128/400 |
| 4,259,961 A | 4/1981 | Hood, III |
| 4,473,637 A | * 9/1984 | Guibert ........................ 435/1 |
| 5,014,695 A | * 5/1991 | Benak et al. ................ 128/400 |
| 5,051,562 A | 9/1991 | Bailey et al. |
| 5,241,951 A | 9/1993 | Mason et al. ............... 607/104 |
| 5,507,792 A | 4/1996 | Mason et al. ............... 607/104 |
| 5,586,438 A | 12/1996 | Fahy ............................. 62/78 |
| 5,591,220 A | 1/1997 | Mahawili .................... 607/104 |
| 6,046,046 A | 4/2000 | Hassanein ................ 435/284.1 |
| 6,100,082 A | 8/2000 | Hassanein ................ 435/284.1 |

FOREIGN PATENT DOCUMENTS

| | | |
|---|---|---|
| DE | G 89 11 429.9 | 9/1989 |
| GB | 2 040 169 A | 11/1999 |

OTHER PUBLICATIONS

PCT Search Report.

* cited by examiner

*Primary Examiner*—Henry Bennett
*Assistant Examiner*—Sabrina Dagostino
(74) *Attorney, Agent, or Firm*—Peter F. Corless; Lisa S. Hazzard; Edwards & Angell, LLP (57) ABSTRACT

A device and method are provided for maintaining donor organs at reduced temperatures ex vivo, in particular while the organ is being implanted in the recipient, and until reperfusion of the organ. By maintaining the organs at reduced temperatures, the potential for external warming of the organ and ischemic injury is reduced and graft performance and survival is improved.

31 Claims, 9 Drawing Sheets

HEART, FRONT VIEW

The Heart: Outside

FIG. 9A

HEART, SECTION THROUGH THE MIDDLE

The Heart: Inside

FIG. 9B

KIDNEY: BLOOD SUPPLY / URETER

THE KIDNEYS

TRANSPLANT ORGAN EXTERNAL COOLING SYSTEM

The present application claims the benefit of U.S. provisional application No. 60/183,093, filed on Feb. 17, 2000, incorporated herein by reference.

FIELD OF THE INVENTION

The present invention relates to an improved apparatus and method for preserving organs for organ transplantation. More particularly, the present invention relates to an apparatus and method that maintains the organ at optimal temperatures ex vivo until reperfusion, thereby preventing external warming of the organ and ischemic injury, and thereby improving graft performance and survival.

BACKGROUND

Over the past 45 years, great strides have been made in organ transplantation. Improved organ preservation techniques, solutions, and apparatus have made it possible to preserve organs hours to days after removal of the organs from the donor body, thereby allowing for transportation of donor organs to recipients at great distances away.

One current technique for preserving a donor organ involves core cooling the organ to 4° C. in situ with preservation solution just prior to removal from a donor cadaver. Cooling the organ to 4° C. results in hypothermic cellular metabolic arrest, wherein the organ is in a non-functioning state. The organ is then stored for transport on ice or in a preservation chamber that maintains the organ at approximately 4° C. and in a metabolically inactive state. Once an organ arrives at its ultimate destination, and the recipient has been prepared, the organ is removed from ice or the preservation chamber and sewn into place in the recipient. This method is described in, for example, U.S. Pat. No. 3,810,367. While this method allows for the transport of donor organs, there are drawbacks. During the period when the organ is "out of ice", prior to reperfusion (e.g. liver 40 to 90 minutes, kidney 25 to 60 minutes, pancreas 25 to 60 minutes), the organ begins to warm up, from the outside toward the center, due to exposure to a combination of ambient (22° C.) and recipient body temperature (37° C.). As a result, the organ returns to its functioning metabolic demands. However, since the organ is not yet connected to the recipient's blood supply and can not receive metabolic substrate, ischemic injury ensues leading to the death of cells, functional components of the tissue, and the liberation of toxic substances. This injury recapitulates what occurs in tissue deprived of oxygen usually due to obstruction of the arterial blood supply or inadequate blood flow leading to hypoxia in the tissue. Ischemia results in irreversible damage to the organs. The process of "out of ice" warming is particularly injurious to the kidney due to the fact that the outer region of the kidney, called the cortex, contains the most important functional elements and this outer area is exposed to the most rapid increase in temperature and ischemic injury. Prolonged "out of ice" time has been associated with poor long-term function and an increased incidence of primary nonfunction of kidney, heart, liver, lung and pancreas allografts.

Recently, techniques and apparatus have been used which maintain the donor organ in an in vivo-like state during transport. Such techniques and apparatus are described in, for example, U.S. Pat. Nos. 6,046,046, 6,100,082, and 5,586,438 which describe, generally, an apparatus that provides a continuous flow of perfusate to the organ. These apparatus may further include a reduced temperature preservation chamber for holding and maintaining the organ at a reduced temperature. However, these techniques and apparatus require that the organ be disconnected from the perfusion apparatus and removed from the reduced temperature preservation chamber while the organ is placed into the recipient's body and sewn into place. This results in warming and ischemia.

It is often difficult to predict which organs will take longer to implant and, thus, it would be advantageous to externally cool all organs until they are sewn into place in the recipient's body to prevent this warming up process. Further, the relationship between tissue injury and time "out of ice" appears to be linear. Thus, because warm ischemia produces a graded injury, reducing the "out of ice" time to essentially zero would result in significant theoretical benefits in preserving the functional units of the organs.

SUMMARY OF THE INVENTION

The present invention provides an apparatus and method for ex vivo preservation of donor organs prior to implantation in a recipient body. More particularly, the apparatus and method of the present invention maintains a donor organ at a reduced temperature while the organ is sewn into place in the recipient's body (i.e. until reperfusion). By maintaining the organ at a suitable reduced temperature, the potential for warming and ischemia are reduced.

When used herein, a "reduced temperature" refers to a temperature below room temperature that can minimize ischemic damage to an organ, preferably a temperature approaching 4° C., such as below about 10° C. or 15° C., more preferably within about 1, 2 or 3° C. of 4° C.

An exemplary embodiment of the apparatus includes a sleeve or blanket for receiving a donor organ and a temperature controlling mechanism for regulating the temperature of the sleeve or blanket. The donor organ is wrapped in the temperature regulated sleeve or blanket, which, in turn, maintains the organ at a desired temperature. Various temperature controlling mechanisms are well-known and, thus, although described below with reference to a preferred embodiment, the general features of the temperature controlling mechanism may be in accordance with conventional temperature controlling mechanisms.

The sleeve or blanket is preferably sufficiently non-rigid to envelope and directly contact multiple surfaces of the three-dimensional organ. Thus, the sleeve or blanket can be wrapped around the three-dimensional organ. Less preferred, although within the scope of the invention, is a more rigid sleeve or blanket that may not contact multiple organ surfaces.

In one embodiment, the temperature controlling mechanism comprises circulating fluid, which regulates the temperature of the sleeve or blanket. In specific embodiments, the sleeve or blanket has an internal pathway for the circulation of cooling fluid. Cooling fluid enters the sleeve or blanket through an entrance port in the sleeve or blanket, flows through the internal pathway, and then exits the sleeve or blanket through an exit port. In one embodiment, the cooling fluid is maintained in a reservoir and a pump circulates the fluid through the internal pathway of the sleeve or blanket. The fluid may be disposed of or returned to the reservoir for recirculation through the sleeve or blanket. The circulating fluid may be cooled within the reservoir or, in some embodiments, a cooling mechanism may be located in the pathway from the reservoir to the entrance port to cool the fluid prior to entering the sleeve or blanket. In some embodiments heating fluid may be circulated through the sleeve or pad rather than or in addition to cooling fluid. In such an embodiment, the fluid may be heated within the reservoir or heated prior to entering the sleeve or blanket.

A method for maintaining donor organ at optimal temperatures until reperfusion is also disclosed. The method comprises providing an apparatus having a donor organ receiving portion and a temperature controlling mechanism for regulating the temperature of donor organ receiving portion. More particularly, the method comprises removing a donor organ from a donor body and transporting the donor organ to the operating site using conventional means. For example, the organ for transplantation may first be core cooled to 4° C. in situ with preservation solution just prior to removal from a donor, thereby inducing hypothermic metabolic arrest. The non-functioning organ is then placed in a preservation container that maintains the organ at approximately 4° C. while the organ is transported to the operating site. Once an organ has arrived at the operating site, the recipient is prepared and the organ is removed from the storage container. The organ is then immediately placed in the donor organ receiving portion of the present apparatus with the vascular pedicle of the organ protruding from the apparatus. A temperature controlling mechanism maintains the organ receiving portion at a temperature of hypothermic metabolic arrest, which maintains the temperature of the donor organ at a temperature of hypothermic metabolic arrest while the organ is sewn into place in the recipient and while the vascular pedicle is connected to the recipient's blood vessels. By maintaining the organ at a temperature of hypothermic arrest during implantation and until reperfusion, the potential for warming of the organ and ischemic damage is reduced.

The apparatus of the invention may provide beneficial effects for a range or organs, including solids organs of the human chest and abdominal regions, such as for use in connection with the transplant of a kidney, liver, lung, heart or pancreas. The cooling apparatus of the invention also will be useful for the transplant of other organs such as appendages e.g. human hand, foot, or finger. As referred to herein, the term appendages is inclusive of hands, feet, fingers, toes, etc.

Other aspects and embodiments of the invention are discussed infra.

DETAILED DESCRIPTION OF THE INVENTION

Referring now to the various figures of the drawing, wherein like reference characters refer to like parts, there is shown in FIGS. 1–8 various views of an apparatus 1, in accordance with the invention, wherein the apparatus 1 maintains a donor organ at reduced temperatures until the organ is sewn into place in the recipient's body (i.e. until reperfusion), thereby reducing the potential for external warming of the organ and ischemia, and thereby improving graft performance and survival.

Figure 1:
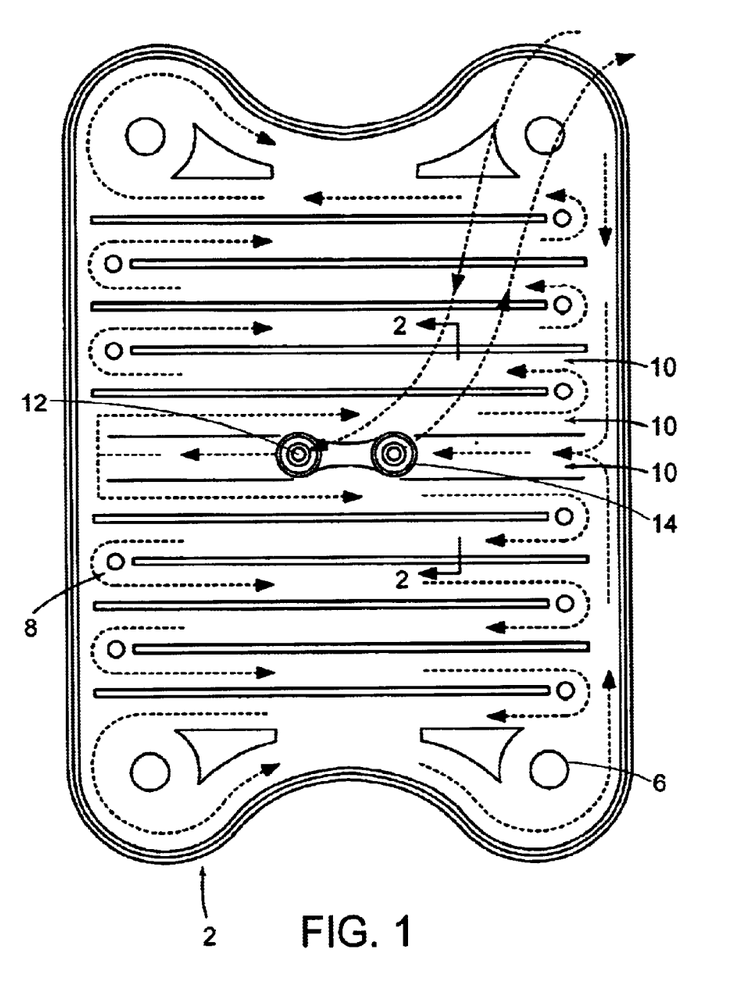
FIG. 1 shows a top view of the apparatus in an open position in accordance with an embodiment of the present invention.

In a preferred embodiment, the apparatus 1 includes an organ receiving portion such as, for example, a sleeve or blanket 2, and a temperature controlling mechanism for maintaining the sleeve or blanket 2 at a desired temperature. When in an open position, as shown in FIG. 1, the sleeve or blanket 2 is generally flat in shape with an inner surface 5 and an outer surface 6. In use, the donor organ is placed on the inner surface 5 and the sleeve or blanket 2 is wrapped about the donor organ, as shown in FIGS. 2–8.

Because the sleeve or blanket 2 contacts the organ directly and is in the sterile field, the entire sleeve or blanket 2 is sterile as well as a portion of the tubing connecting the sleeve or blanket to the temperature controlling mechanism. In one embodiment, the sleeve or blanket 2 and tubing are reusable and sterilized between uses. Alternatively, the entire sleeve or blanket 2 and tubing are disposable and thrown out between uses. Similarly, a disposable sterile cover (not shown) may be placed over the sleeve or blanket 2, thereby encasing the sleeve or blanket 2 and providing a sterile unit. The sterile cover is placed over the sleeve or blanket 2 prior to use. After use, the sterile cover is removed and disposed of. The sleeve or blanket 2 is then reused by simply placing a new sterile cover over the sleeve or pad 2.

As shown in FIG. 1, in a preferred embodiment, the sleeve or blanket 2 can have an internal pathway 8, shown by the dotted lines, for the circulation of cooling fluid. For example, the interior of the sleeve or blanket 2 may include a plurality of internal linking cells or canals 10 that allows for the rapid and free flow of circulating fluid. These linking cells or canals 10 may be easily formed by, for example, connecting the inner surface 5 to the outer surface 6 along portions of the length or width of the sleeve or blanket 2. Alternatively, a tube or similar device can be located within the sleeve or blanket 2 to form the internal pathway 8. The internal pathway 8 is preferably lined with a waterproof material to prevent leakage of circulation fluid. As cool fluid is circulated through the internal pathway 8, the sleeve or blanket 2 is cooled and, thus, an organ wrapped within the sleeve or blanket 2 will, likewise be cooled. Similar sleeves or blankets are disclosed in, for example, U.S. Pat. Nos. 5,591,220, 5,507,792 and 5,241,951, which are incorporated herein by reference.

Figure 2:
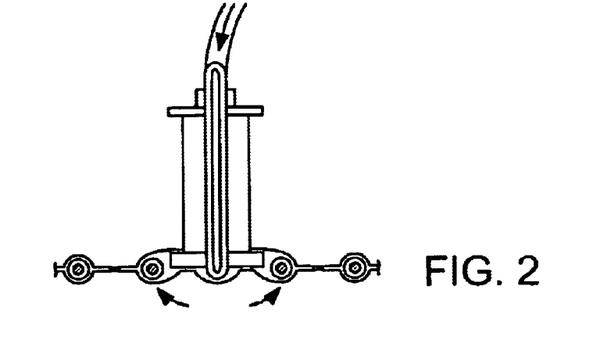
FIG. 2 shows a side view of the apparatus of FIG. 1 in a wrapped position.
Figure 3:
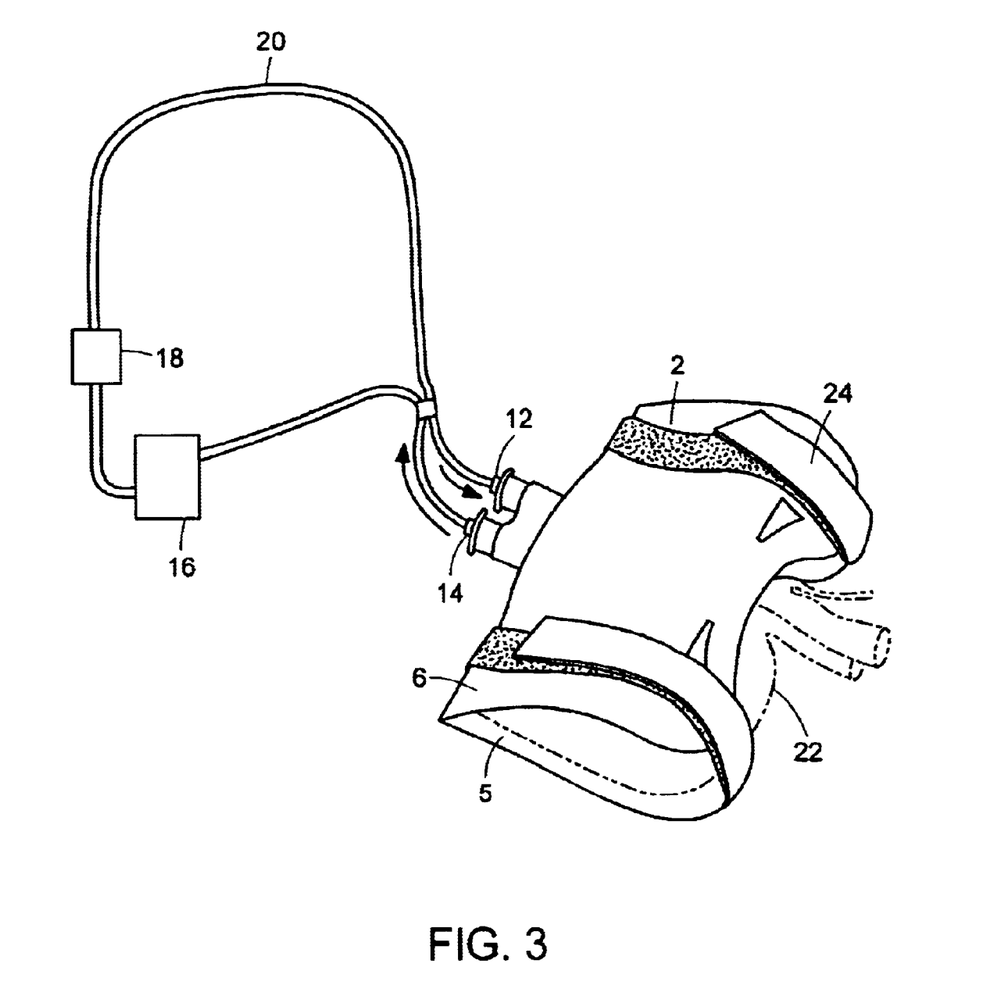
FIG. 3 is an isometric view of the apparatus of FIG. 1 as used on an organ and connected to a cooling pump and reservoir.

As shown in FIGS. 1–8, the sleeve or blanket 2 may include an entrance port 12 and exit port 14 in fluid communication with the internal pathway 8 through which the circulating fluid enters and exits the sleeve or blanket 2. A fluid source, for providing circulating fluid, is in fluid communication with the entrance port 12. As shown in FIG. 3, tubing 20 or the like may provide the fluid communication between the fluid source and entrance port 12. In one embodiment, circulating fluid, preferably sterile, is held in a reservoir 16, and is pumped from the reservoir 16 to the entrance port 12 by use of a pump 18. Any type of conventional motor or manual driven pump could be used to transport the circulating fluid from reservoir 18 through the sleeve or blanket 2 at various pressures. The fluid would, thus, be pumped from the reservoir 16, through the tubing 20 and into the sleeve or blanket 2 through the entrance port 12.

When the apparatus 1 is used to maintain the donor organ at reduced temperatures, the circulating fluid must be cool and, thus, the temperature controlling mechanism is a cooling mechanism that cools the circulating fluid before the fluid enters the internal pathway 8. In one embodiment, the cooling mechanism is located at the reservoir 16, such that the circulating fluid is cooled within the reservoir 16. In this embodiment, the reservoir 16 is preferably insulated and covered to assist in maintaining the fluid in the reservoir 16 at a desired temperature. In another embodiment, the cooling mechanism may be, for example, a cooling coil, or similar cooling mechanism, located in the pathway from the reservoir 16 to the entrance port 12. In this embodiment, the reservoir 16 may be insulated and covered or, if desired, may simply be an open container, such as a bucket.

In some embodiments, it may be desirable to circulate heating fluid through the sleeve or blanket 2 in addition to cooling fluid. In such an embodiment, the circulating fluid must be heated and, thus, the temperature controlling mechanism includes a heating mechanism that heats the circulating fluid before the fluid enters the internal pathway 8. For example, in addition to a cooling mechanism described above, a heating mechanism may further be located within the reservoir 16. In this embodiment, the reservoir 16 is preferably insulated and covered to assist in maintaining the fluid in the reservoir 16 at a desired temperature. In another embodiment, the heating mechanism may be, for example, a heating coil, or similar heating mechanism, located in the pathway from the reservoir 16 to the entrance port 12. In this embodiment, the reservoir 16 may be insulated and covered or, if desired, may simply be an open container, such as a bucket.

After the fluid passes through the internal pathway 8 of the sleeve or blanket 2, the fluid then exits the sleeve or blanket 2 through the exit port 14. The fluid exiting the exit port 14 may then be disposed of or recirculated through the sleeve or blanket 2. In one embodiment, the fluid exits exit port 14 through tubing 20, which extends from the exit port 14 to the reservoir 16. The fluid is then pumped from the reservoir 16, through the tubing 20 and is recirculated through internal pathway 8 of the sleeve or blanket 2, as shown in FIG. 3.

In a preferred embodiment, a window (not shown), through which the flow of circulating fluid may be viewed, is located in the pathway between the fluid source or reservoir 16 and the entrance port 12. Thus, it is possible to monitor the flow of circulating fluid and ensure that the flow is not ceased during use. In another preferred embodiment, tubing 20, which provides the fluid communication between the fluid source or reservoir 16 and entrance port 12, is clear. Thus, one may easily monitor the flow of circulating fluid through the tubing 20 to ensure that the flow is not ceased during use.

A thermometer may be located in the flowpath after the circulating fluid is cooled so that the temperature of the cooling fluid may be monitored and adjusted as required. A thermometer may also be located along the inner surface 5 of the sleeve or blanket 2 to ensure that the portion of the apparatus contacting the donor organ is maintained at a proper temperature.

Preferably, the sleeve or blanket 2 wraps around and surrounds the donor organ (e.g. liver, kidney, heart, lung or pancreas), as shown in FIGS. 3–8, allowing the vascular pedicle 22 to protrude. To allow for wrapping of the sleeve or blanket 2 about the donor organ, the sleeve or blanket 2 is made of a pliable material. Some suitable materials include soft plastics, fabric and similar materials. Additionally, materials conventionally used in fabricating sequential compression devices (SCS), which are adjustable, pneumatic stockings placed on patients legs during surgery, may also be used in fabricating the sleeve or blanket 2.

To allow heat exchange between the cooling fluid and the donor organ, the inner surface 12 of the sleeve or blanket 2 is fabricated of a material that allows for heat transfer through the material. When used, the sterile cover, which lines the sleeve or blanket 2, is likewise fabricated of a material that allows for heat transfer through the material. Further, to prevent the cooling fluid from being warmed by the temperature of the external environment, the sleeve or blanket 2 is preferably insulated by providing, for example, an outer surface 12 fabricated of a heat-insulative material to minimize heat exchange or, for example, by providing a layer of material between the internal pathway 8 and external environment, wherein the layer of material is fabricated of a heat-insulative material to minimize heat exchange between the cooling fluid and the external environment.

Various temperature controlling mechanisms are well-known and, thus, although described with reference to a preferred embodiment, the temperature controlling mechanism is any of a number of devices, mechanisms or arrangements known to those skilled in the art. Thus, rather than utilize an internal pathway 8 with circulating fluid, the sleeve or blanket 2 may, for example, have a refillable internal compartment for holding a precooled or preheated substance or the sleeve or blanket 2 may contain an electrical cooling or heating element.

Figure 4:
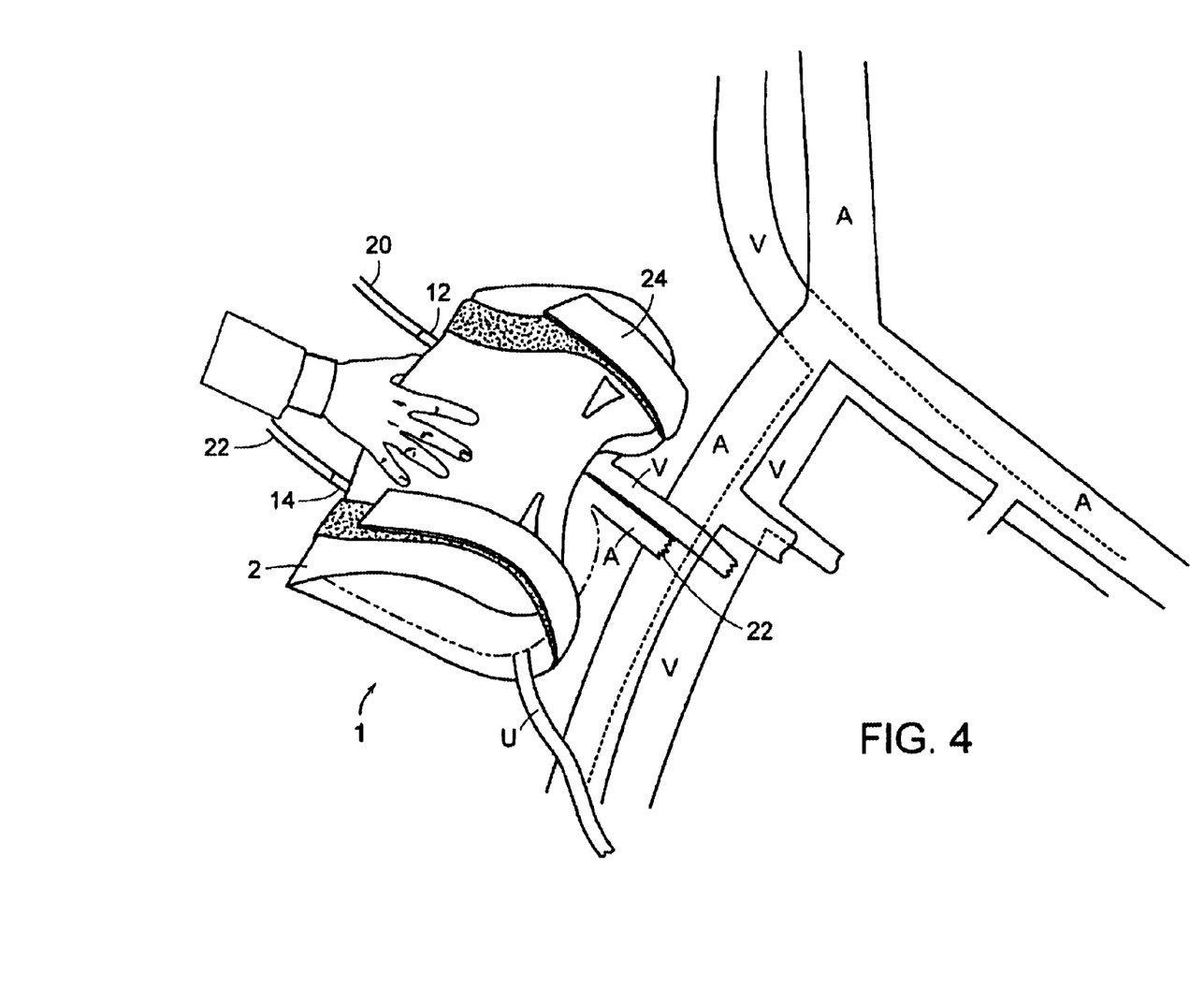
FIG. 4 shows an isometric view of the apparatus of FIG. 1 as used in the operating room.
Figure 5:
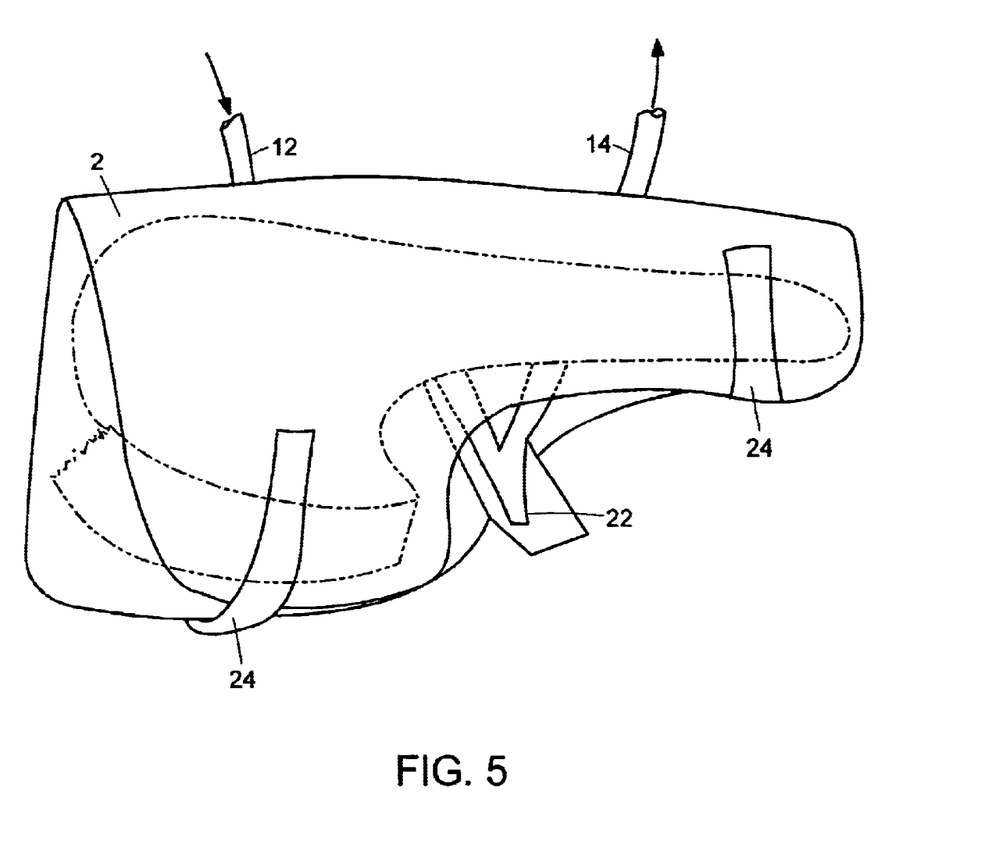
FIG. 5 shows a view of the apparatus of FIG. 1 as used on a pancreas.
Figure 6:
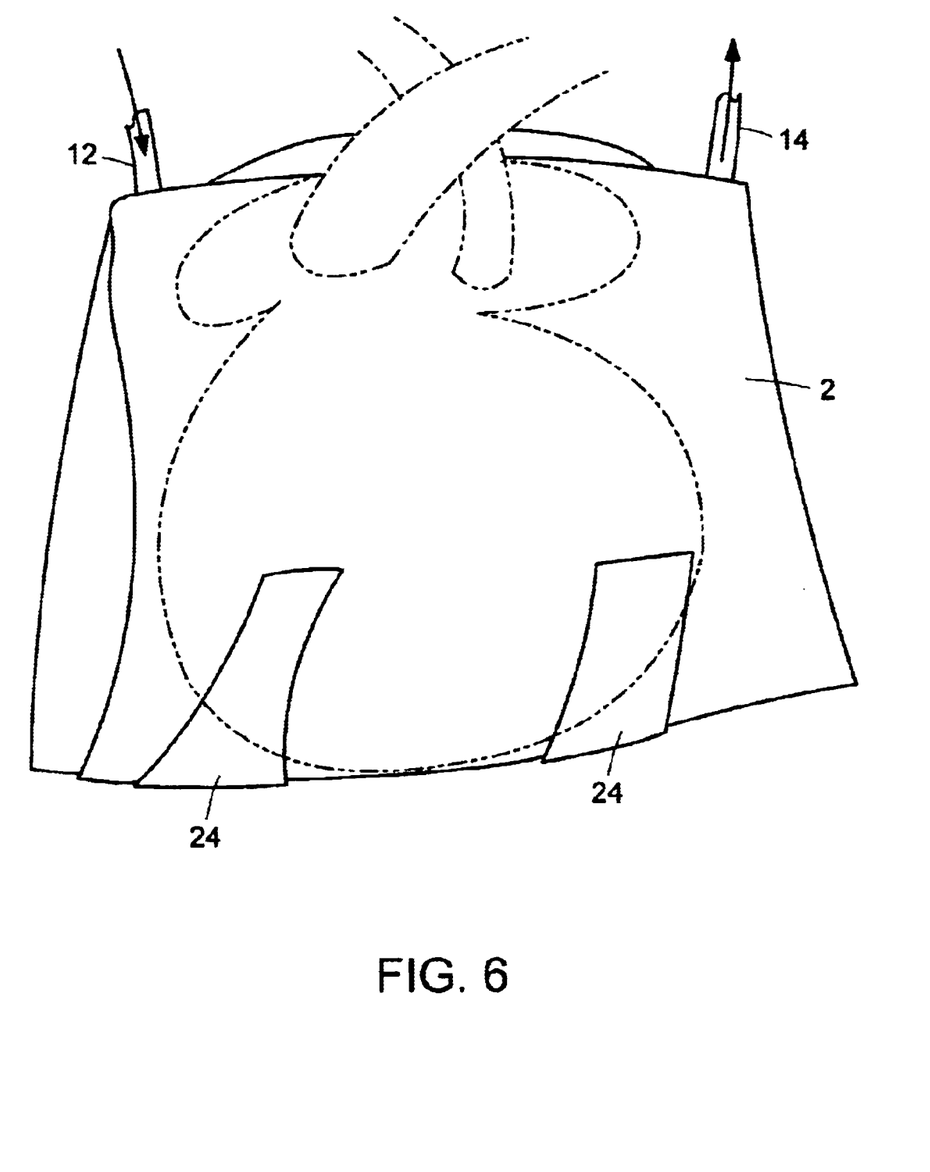
FIG. 6 shows a view of the apparatus of FIG. 1 as used on a heart.

In a preferred embodiment, the sleeve or blanket 2 is adjustable and may be used on various organs including, for example, the liver, kidney, heart, lung and pancreas. The sleeve or blanket 2 may also be custom built for individual organ types. After the donor organ is placed on the inner surface 5 of the sleeve or blanket 2, the sleeve or blanket 2 is wrapped about the organ. The sleeve or blanket 2 may, then, be secured about the organ by fasteners 24 such as, for example, Velcro strips (as shown in FIGS. 2 and 4), snaps, buttons, buckles or similar fasteners that keep the organ wrapped securely in the sleeve or blanket 2 and allow the sleeve or blanket 2 to be removed after the pedicle has been joined to the recipients blood vessels.

Figure 7:
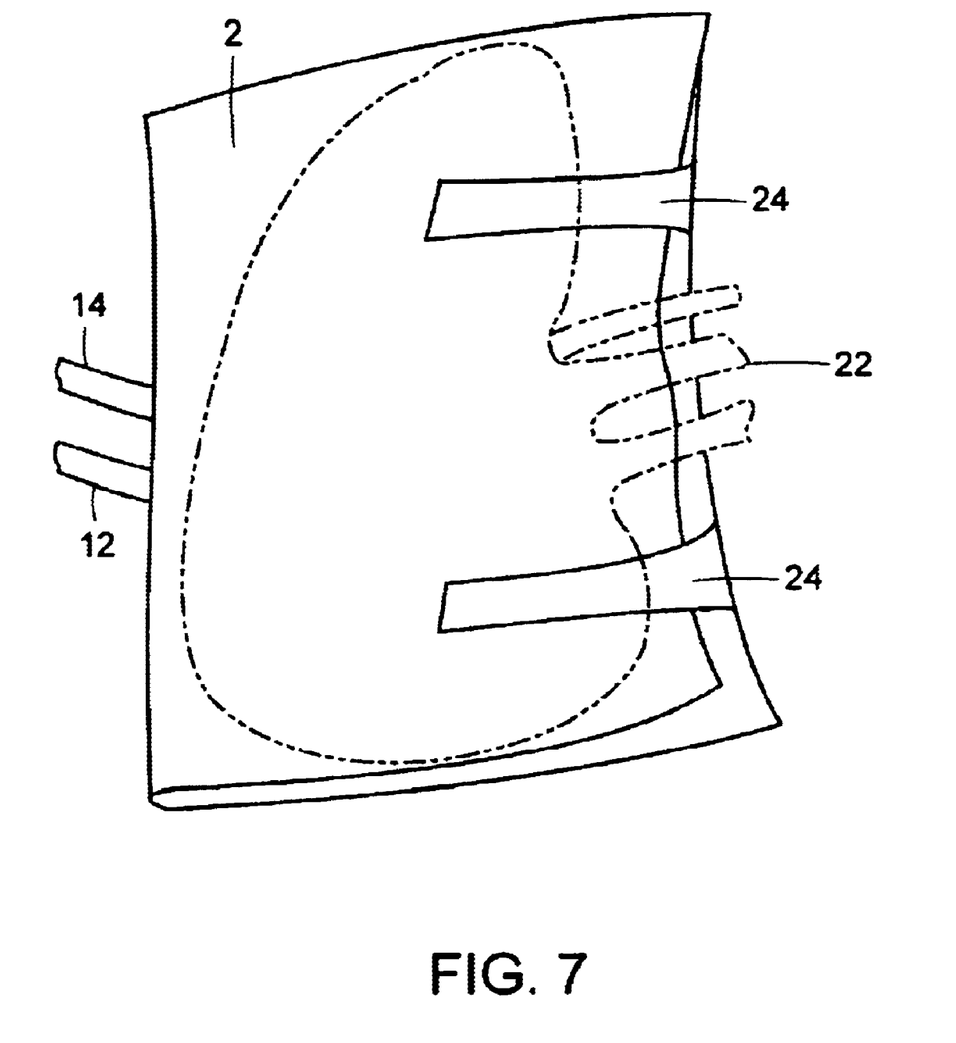
FIG. 7 shows a view of the apparatus of FIG. 1 as used on a lung.
Figure 8:
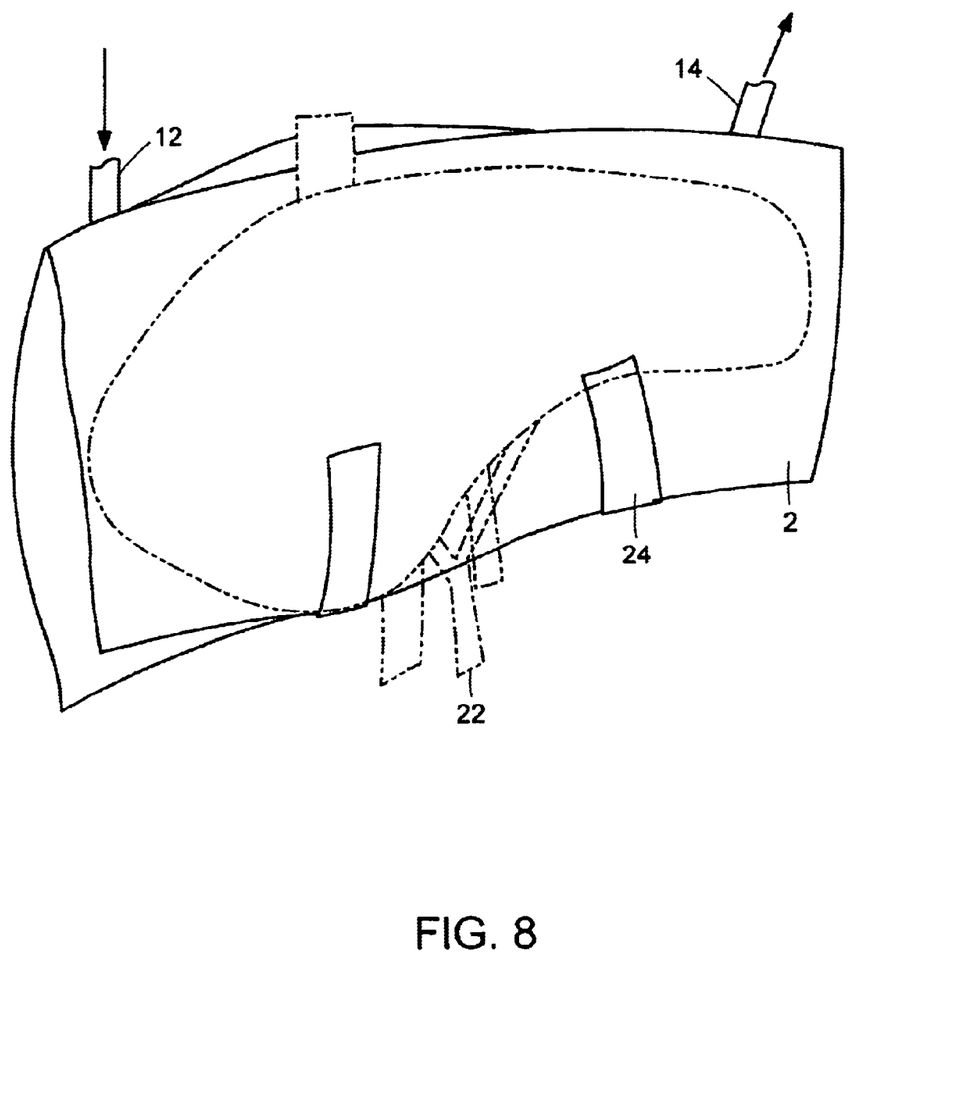
FIG. 8 shows a view of the apparatus of FIG. 1 as used on a liver.
Figure 9A:
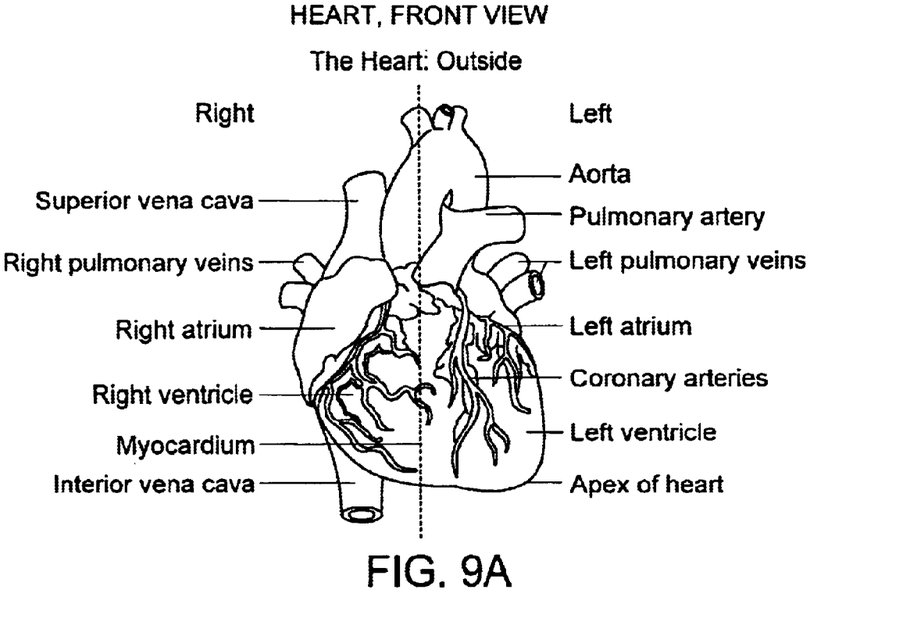
FIGS. 9a and 9b show outer and inner views of the heart.
Figure 9B:
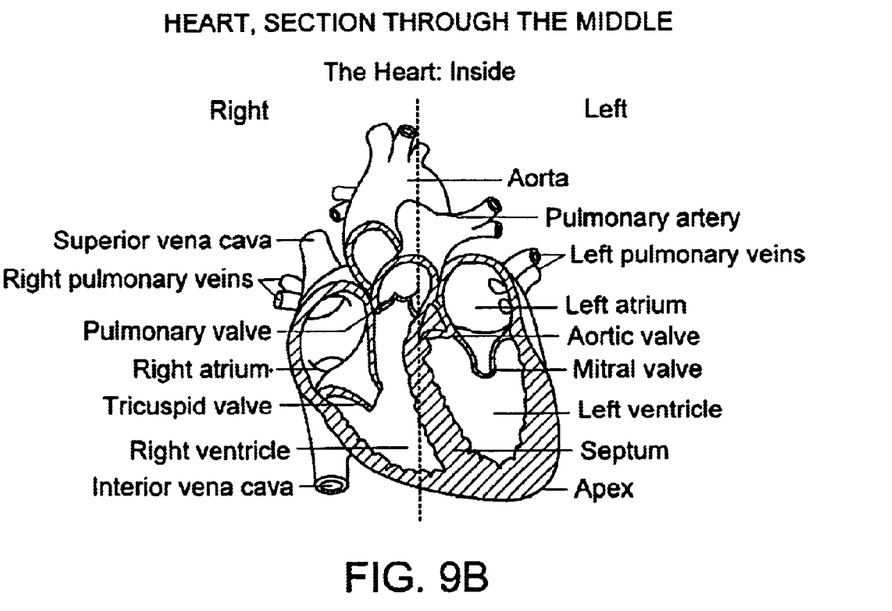
Figure 10A:
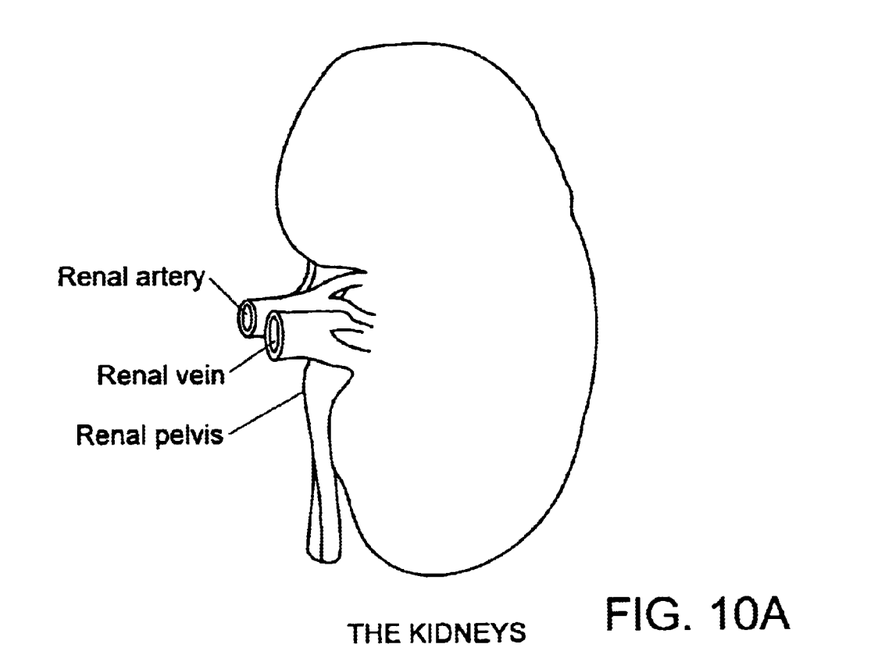
FIGS. 10a and 10b show outer and inner views of a kidney.
Figure 10B:
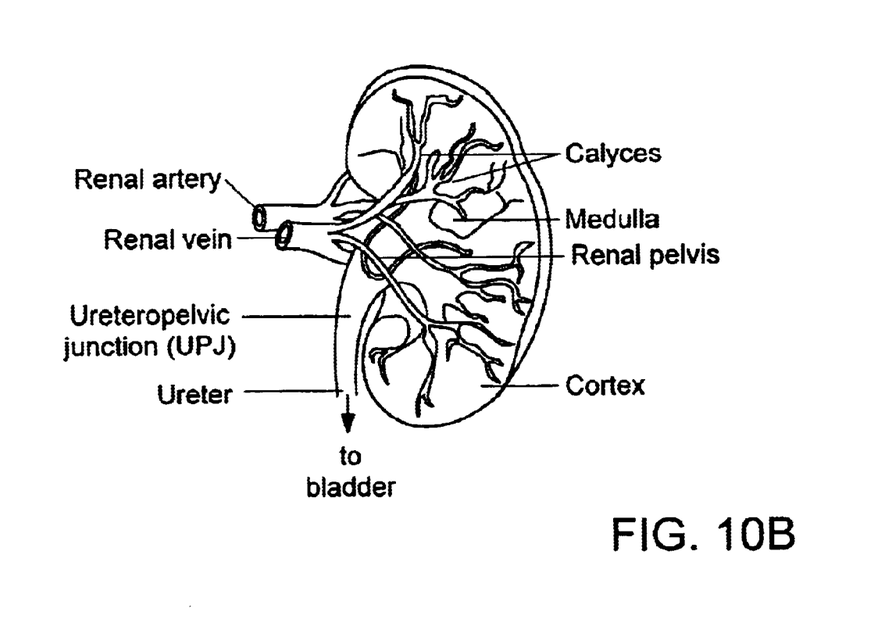

The apparatus 1 is generally used by the following procedure: an organ for transplantation is core cooled to about 4° C. in situ with preservation solution just prior to removal from a donor. This temperature is maintained while the organs are stored for transport on ice or in a preservation chamber, described in, for example, U.S. Pat. Nos. 3,810, 367, 6,046,046, 6,100,082, and 5,586,438. Once the organ arrives at the operating site, the human recipient is prepared and the organ is removed from ice or the preservation chamber. The organ is then placed on the inner surface 5 of the sleeve or blanket 2, or, if used, on the disposable cover lining the sleeve or blanket 2. The sleeve or blanket 2 is wrapped about the organ allowing the vascular pedicle 22 to protrude. Fasteners 24 may then be secured to hold the sleeve or blanket 2 wrapped tightly about the organ and allow easy removal of the sleeve or blanket 2 after the organ is sewn into place in the recipient. Preferably, the sleeve or blanket 2 is pre-cooled prior to use by continuously circulating cooling fluid through the sleeve or blanket 2 until the sleeve or blanket 2 is at the appropriate temperature. While the donor organ is wrapped in the sleeve or blanket 2, cooling fluid is continuously circulated through the sleeve or blanket 2 to maintain the sleeve or blanket 2 and the organ at a reduced temperature as the pedicle is joined to the recipient's blood vessels, and until reperfusion. In some cases, for example during kidney and pancreas transplants, while the pedicle is joined to the recipient's blood vessels, the organ wrapped in the sleeve or blanket is preferably suspended above the patient by a holding mechanism or manually, as shown in FIG. 7. It is preferred that the organ wrapped in the sleeve or blanket is suspended such that the vascular pedicle 22 is held under tension as it is reconnected to the recipient's blood vessels. After the pedicle is joined, the fasteners 24 are unfastened, the sleeve or blanket 2 is removed from the organ, the organ is lowered into the patient and the operation is completed.

In another embodiment, the apparatus I may further be used as the preservation chamber or in connection with conventional preservation chambers to transport the organ from the donor to the recipient. Thus, the apparatus would be generally used by the following procedure: an organ for transplantation is core cooled to about 4° C. in situ with preservation solution just prior to removal from a donor. The removed organ is then placed on the inner surface 5 of the sleeve or blanket 2, or, if used, on the disposable cover lining the sleeve or blanket 2. The sleeve or blanket 2 is wrapped about the organ allowing the vascular pedicle 22 to protrude. Fasteners 24 may then be secured to hold the sleeve or blanket 2 wrapped tightly about the organ. Preferably, the sleeve or blanket 2 is pre-cooled prior to use by continuously circulating cooling fluid through the sleeve or blanket 2 until the sleeve or blanket 2 is at the appropriate temperature. While the donor organ is wrapped in the sleeve or blanket 2, cooling fluid is continuously circulated through the sleeve or blanket 2 to maintain the sleeve or blanket 2 and the organ at a reduced temperature. If desired, the vascular pedicle may further be connected to a perfusion device (see U.S. Pat. Nos. 6,046,046, 6,100,082, and 5,586,438). The reduced temperature is maintained and, if used, the perfusion device provides a continuous flow of perfusate to the organ while the organ is transported to the operating site. Once the organ arrives at the operating site, the recipient is prepared. At this time, the perfusion device is disconnected. Cooling fluid is continuously circulated through the sleeve or blanket 2 to maintain the sleeve or blanket 2 and the organ at a reduced temperature as the vascular pedicle is joined to the recipient's blood vessels, and until reperfusion. In some cases, while the pedicle is joined, the organ wrapped in the sleeve or blanket 2 is preferably suspended above the patient by a holding mechanism or manually, as shown in FIG. 7. It is preferred that the organ wrapped in the sleeve or blanket is suspended such that the vascular pedicle 22 is held under tension as it is reconnected to the recipient's blood vessels. After the pedicle is joined, the fasteners 24 are unfastened, the sleeve or blanket 2 is removed from the organ, the organ is lowered into the patient and the operation is completed. By using the apparatus 1 of the present invention as the cooling means during transport of the organ, not only is the core of the organ cooled, as is the case with perfusion devices, but also the outer portion of the organ is cooled.

To maintain the organ at an appropriate reduced temperature, the temperature of the cooling fluid preferably approaches 4° C. However, it is to be understood that the temperature of the cooling fluid may vary based on, for example, the materials used in fabricating the sleeve or blanket 2 and the flow rate of the cooling fluid through the sleeve or blanket 2.

Further, to maintain the organ at an appropriate reduced temperature, at least 50%, 60% or 70%, more preferably at least about 80%, still more preferably at least about 90%, 98% or 100% of the surface area of the donor organ contacts the inner surface 12 of the sleeve or blanket 2. However, contact with even smaller amount of the organ surface area with a sleeve or blanket of the invention can provide beneficial cooling, e.g. where the blanket contact less than about 50%, 40%, or 30% of the organ surface area.

It may further be desirable in some applications to use the apparatus 1 to heat the organ in addition to cooling the organ. For example, the apparatus can first be used as a cooling apparatus described above until reperfusion or right before reperfusion. The apparatus may then be used as a heating apparatus to assist in returning the organ to its functioning metabolic demands. Thus, for example, after reperfusion or just prior to reperfusion, the cooling mechanism may be turned off and the heating mechanism turned on. At this time, the bladder, airways or bile duct may be connected. Then, the fasteners 24 are unfastened, the sleeve or blanket 2 is removed from the organ and the operation is completed.

In addition to using the apparatus on donor organs, the apparatus may also be used on appendages or the like, for example, in transporting a severed appendage (e.g. finger, hand, foot, ear) at a reduced temperature to the operating room for reconnection to the human patient's body, or for transplant (e.g. hand or foot).

The present invention also includes kits that comprise one or more apparatus of the invention, preferably packaged in sterile condition. Kits of the invention also may include tubing, sterile covers for use with the apparatus, preferably packaged in sterile condition, and/or written instructions for use of the apparatus and other components of the kit.

Although a preferred embodiment of the invention has been described using specific terms, such description is for illustrative purposes only, and it is to be understood that changes and variations may be made without departing from the spirit or scope of the following claims.

What is claimed is:

1. An apparatus for maintaining a donor organ at a reduced temperature until reperfusion comprising:
    a donor organ receiving portion that envelops the donor organ;
    at least one adjustable, refastenable fastener comprising an elongate strap that wraps about the donor organ receiving portion; and
    a temperature controlling mechanism, whereby the donor organ is contained in the donor organ receiving portion until reperfusion and
    wherein the donor organ receiving portion contacts at least about 70% of the surface area of the donor organ.

2. An apparatus for maintaining a donor organ at a reduced temperature until a vascular pedicle of the donor organ is connected to a recipient's blood supply comprising:
    a donor organ receiving portion; and
    a temperature controlling mechanism,
    whereby the donor organ is contained in the donor organ receiving portion, with the vascular pedicle protruding from the donor organ receiving portion, and the donor organ is maintained at a reduced temperature until the vascular pedicle is attached to the recipient's blood supply and wherein the donor organ receiving portion is provided with refastenable fasteners for securing the donor organ receiving portion about the donor organ, wherein the refastenable fasteners comprise elongate straps that wrap about the donor organ receiving portion and that provide enhanced contact between the donor organ receiving portion and the surfaces of the organ.

3. The apparatus of claim 1 or 2, wherein the reduced temperature is below 10° C.

4. The apparatus of claim 1 or 2, wherein the reduced temperature is about 4° C.

5. The apparatus of claim 1 or 2, wherein the reduced temperature is a temperature of hypothermic metabolic arrest of the organ.

6. The apparatus of claim 1 or 2, wherein the donor organ receiving portion contacts at least about 70% of the surface area of the donor organ.

7. The apparatus of claim 6, wherein the donor organ receiving portion contacts at least about 80% of the surface area of the donor organ.

8. The apparatus of claim 7, wherein the donor organ receiving portion contacts at least about 90% of the surface area of the donor organ.

9. The apparatus of claim 1 or 2, wherein the donor organ receiving portion is a pliable sleeve or blanket that wraps about the donor organ with a vascular pedicle of the donor organ protruding from the sleeve or blanket.

10. The apparatus of claim 9, wherein the fasteners maintain the sleeve or blanket wrapped about the donor organ and allow for unfastening of the sleeve or blanket about the donor organ, adjustment of the sleeve or blanket about the donor organ and refastening about the donor organ and for the easy removal of the sleeve or blanket after reperfusion.

11. The apparatus of claim 9, wherein the sleeve or blanket has an inner surface and an outer surface, whereby the donor organ is placed on the inner surface and the sleeve or blanket wraps about the donor organ.

12. The apparatus of claim 1 or 2, further comprising a disposable, removable sterile cover for encasing the donor organ receiving portion.

13. The apparatus of claim 1 or 2, wherein the temperature controlling mechanism comprises an internal pathway in the donor organ receiving portion through which fluid is circulated.

14. An apparatus of claim 1 or 2 further comprising a heating means for healing the donor organ receiving portion.

15. A medical device kit, comprising the apparatus claim 1 packaged in a sterile form.

16. A method for maintaining a donor organ ex vivo at a reduced temperature until reperfusion comprising placing a donor organ in contact with the apparatus of claim 1 or 2.

17. The method of claim 16, wherein the reduced temperature is below 10° C.

18. The method of claim 16, wherein the reduced temperature is about 4° C.

19. The method of claim 16, wherein the reduced temperature is a temperature of hypothermic metabolic arrest of the organ.

20. The method of claim 16, wherein the donor organ receiving portion contacts at least about 70% of the surface area of the donor organ.

21. The method of claim 20, wherein the donor organ receiving portion contacts at least about 80% of the surface area of the donor organ.

22. The method of claim 21, wherein the donor organ receiving portion contacts at least about 90% of the surface area of the donor organ.

23. The method of claim 16, wherein the donor organ receiving portion is a pliable sleeve or blanket that wraps about the donor organ with a vascular pedicle of the donor organ protruding from the sleeve or blanket.

24. The method of claim 23, further comprising maintaining the sleeve or blanket wrapped about the donor organ by fasteners and removing the organ from the sleeve or blanket by unfastening the fasteners.

25. The method of claim 16, further comprising encasing the donor organ receiving portion with a disposable, removable sterile cover.

26. The method of claim 16, wherein the organ is a solid organ.

27. The method of claim 16 wherein the organ is a kidney, liver, lung, heart or pancreas.

28. The method of claim 16 wherein the organ is a hand, foot, or finger.

29. The method of claim 16, further comprising heating the donor organ after reperfusion or just prior to reperfusion to assist in returning the donor organ to its functioning metabolic demands.

30. The method according to claim 16, further comprising,
    precooling the donor organ receiving apparatus,
    wrapping the donor organ in the apparatus while allowing a vascular pedicle of the donor organ to protrude;
    maintaining the donor organ at a reduced temperature;
    attaching the vascular pedicle to the recipient's blood vessels; and
    removing the organ from the apparatus.

31. The apparatus of claim 1 or 2 wherein the fasteners comprise elongate Velcro strips positioned along an outer surface of the donor organ receiving portion that mate with elongate Velcro straps that wrap about the outer surface of the donor organ receiving portion.

* * * * *